United States Patent [19]
Goble et al.

[11] Patent Number: 5,458,602
[45] Date of Patent: Oct. 17, 1995

[54] SURGICAL DRILL GUIDE

[75] Inventors: E. Marlowe Goble, Logan, Utah; Harold M. Martins, Newton, Mass.; David P. Luman, Logan; Daniel A. Perkins, West Weber, both of Utah

[73] Assignee: Mitek Surgical Products, Inc., Westwood, Mass.

[21] Appl. No.: 180,100

[22] Filed: Jan. 11, 1994

[51] Int. Cl.⁶ ............................................. A61F 2/32
[52] U.S. Cl. ............................................. 606/96; 606/98
[58] Field of Search ..................... 606/96, 86, 87, 606/97, 98, 102, 103, 104

[56] References Cited

U.S. PATENT DOCUMENTS

| | | | |
|---|---|---|---|
| 4,708,139 | 11/1987 | Dunbar, IV | 606/96 |
| 4,739,751 | 4/1988 | Sapega et al. | 606/96 |
| 4,883,048 | 11/1989 | Purnell et al. | 606/96 |
| 4,920,958 | 5/1990 | Walt et al. | 606/103 X |
| 5,112,337 | 5/1992 | Paulos et al. | 606/98 X |
| 5,154,720 | 10/1992 | Trott et al. | 606/96 |
| 5,163,940 | 11/1992 | Bourque | 606/96 |

*Primary Examiner*—Peter A. Aschenbrenner
*Attorney, Agent, or Firm*—Pandiscio & Pandiscio

[57] ABSTRACT

An improved drill guide device is provided for accurately drilling a passageway through bone. The drill guide comprises a support, a curved radial rack, a locator boom movably disposed on the curved radial rack, a drill sleeve and an indexing mechanism. The drill sleeve may be discretely indexed toward the target bone and locked/unlocked in position with a single handed operation.

25 Claims, 13 Drawing Sheets

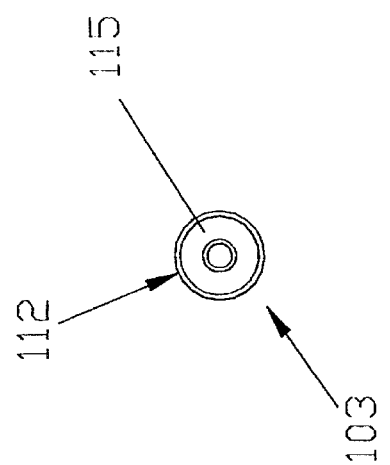
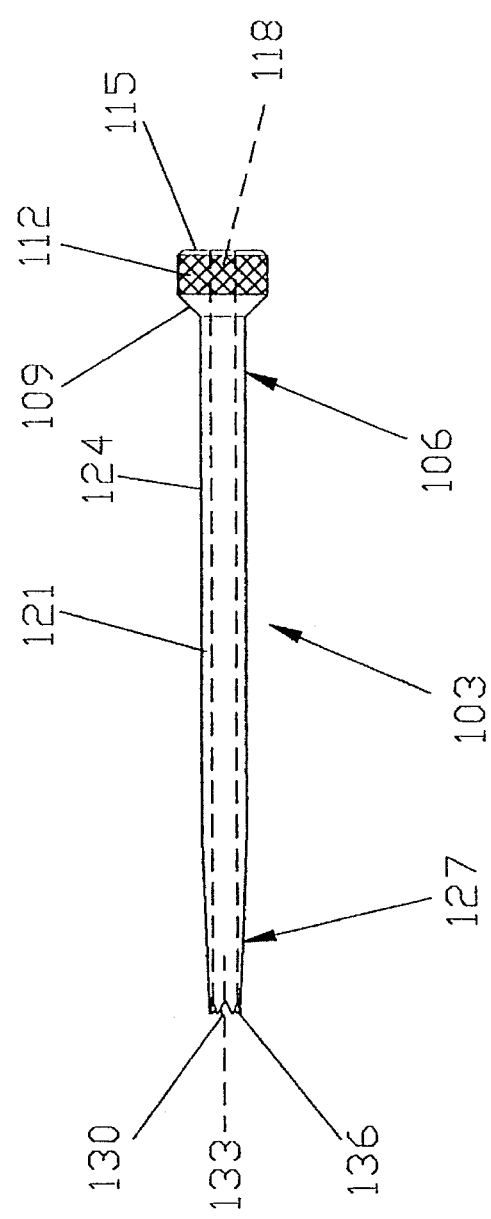
FIG. 6
FIG. 5

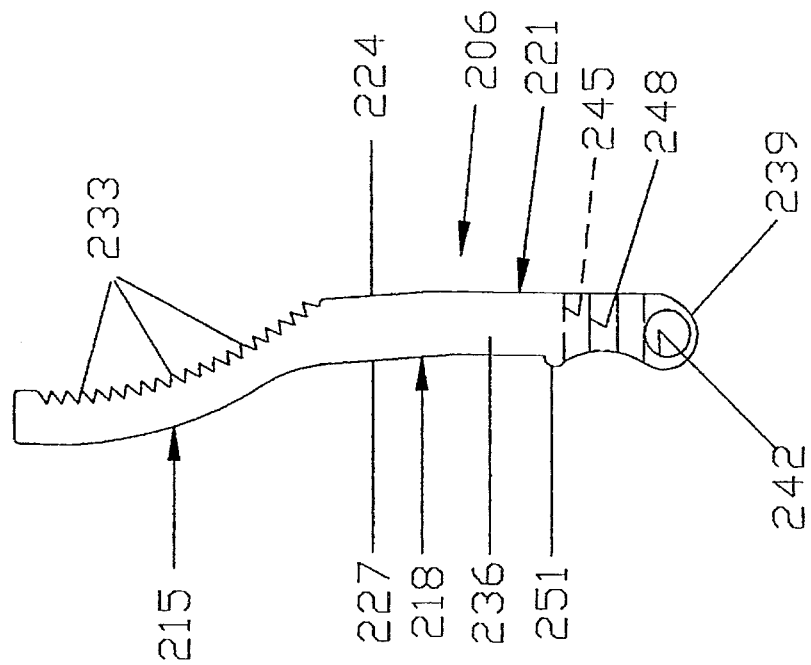
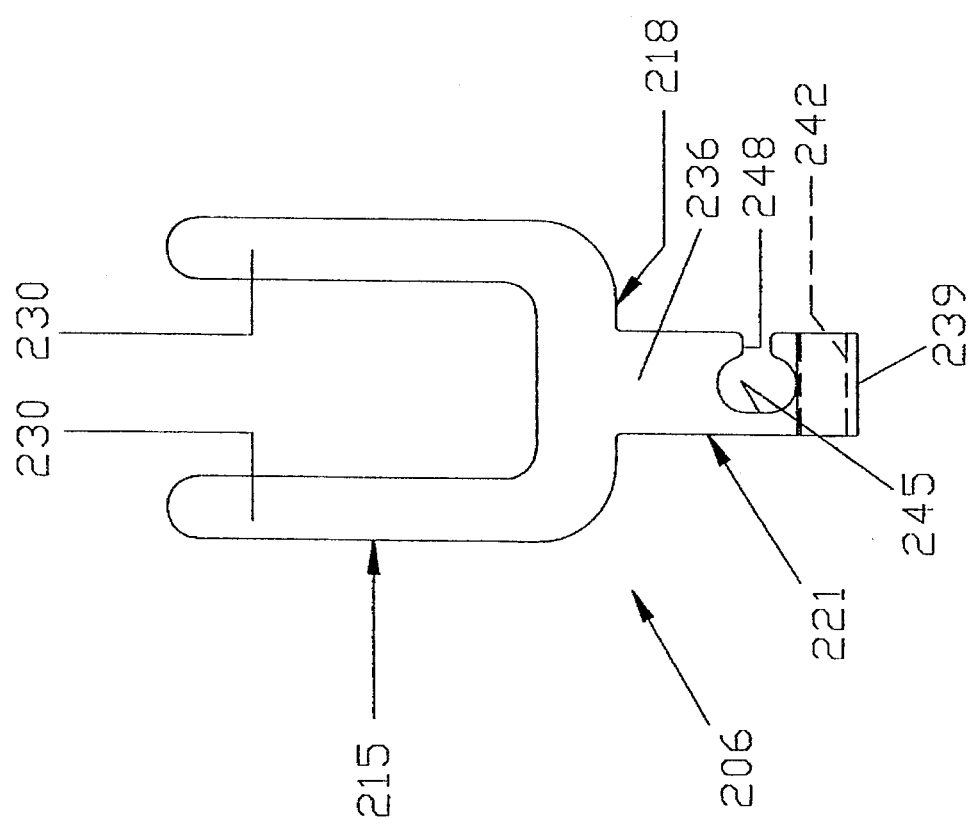

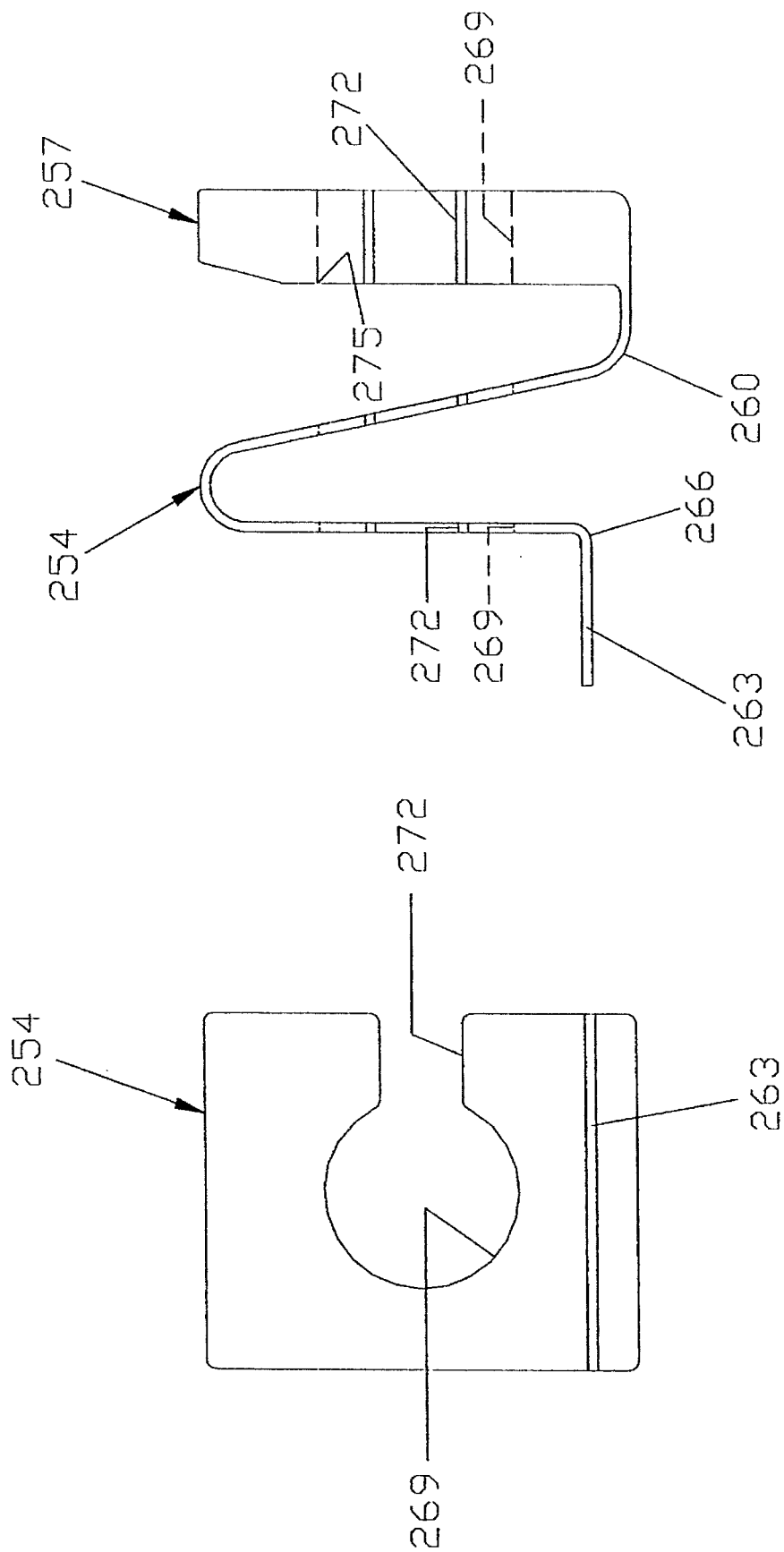

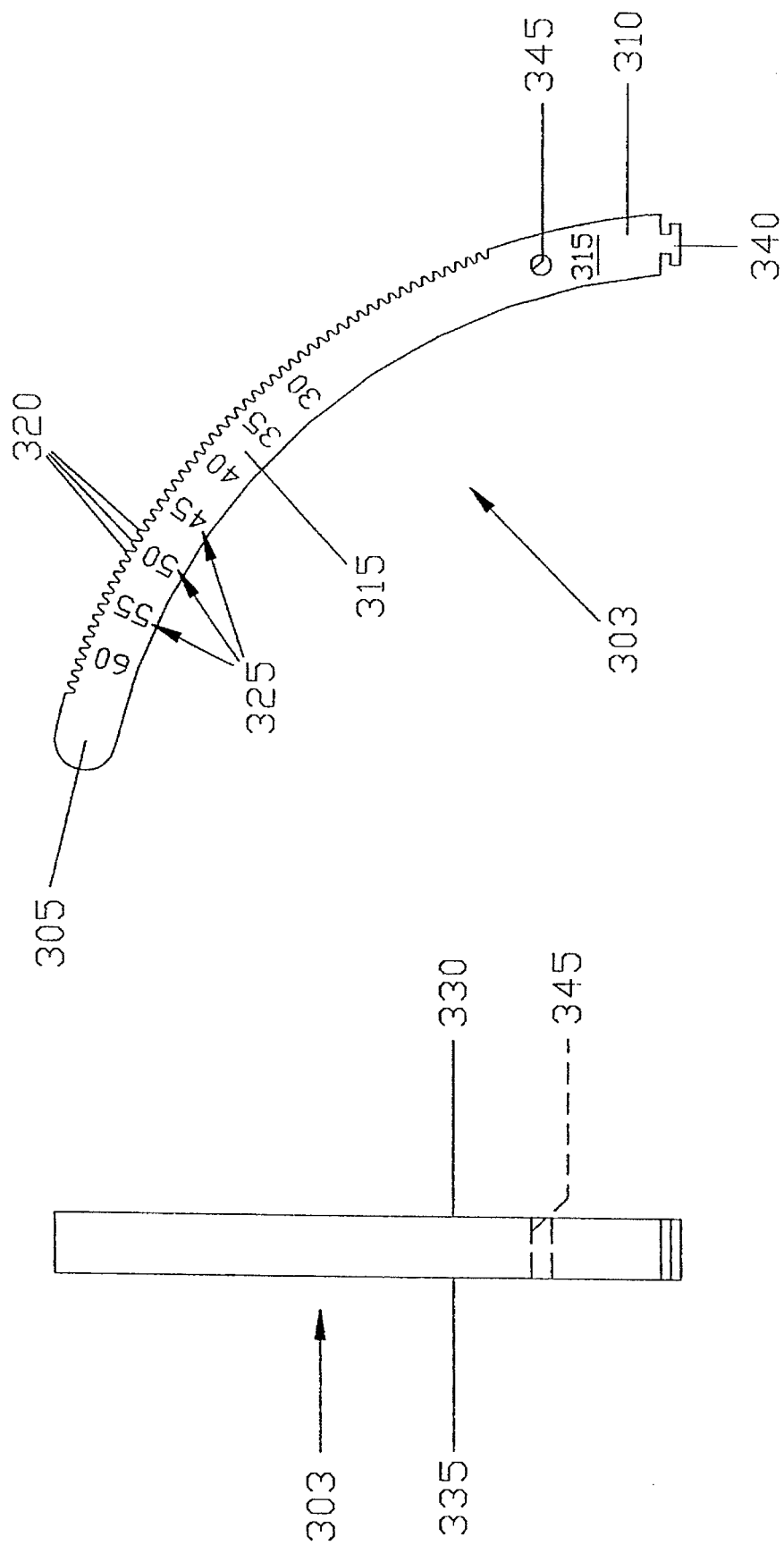

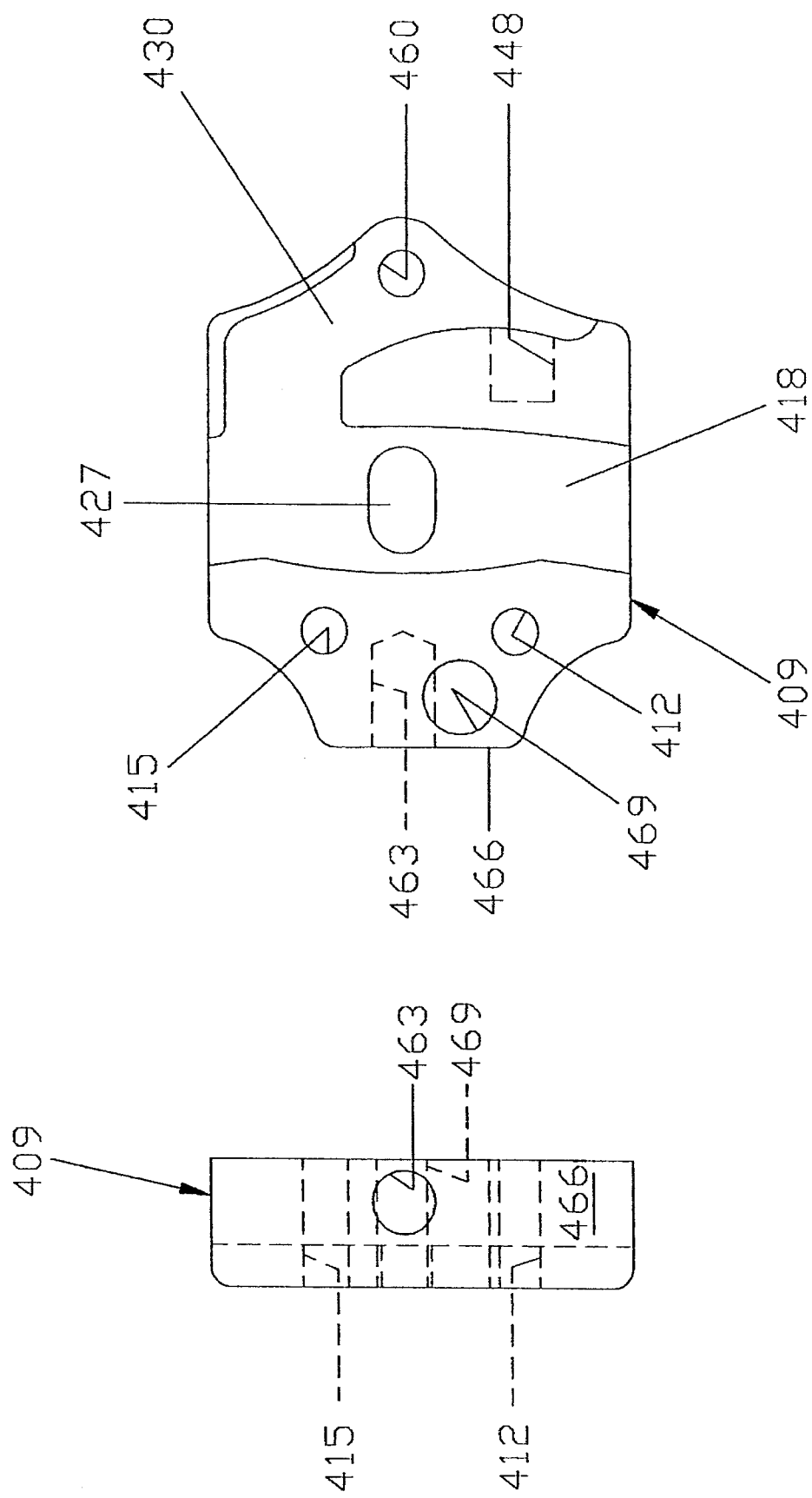

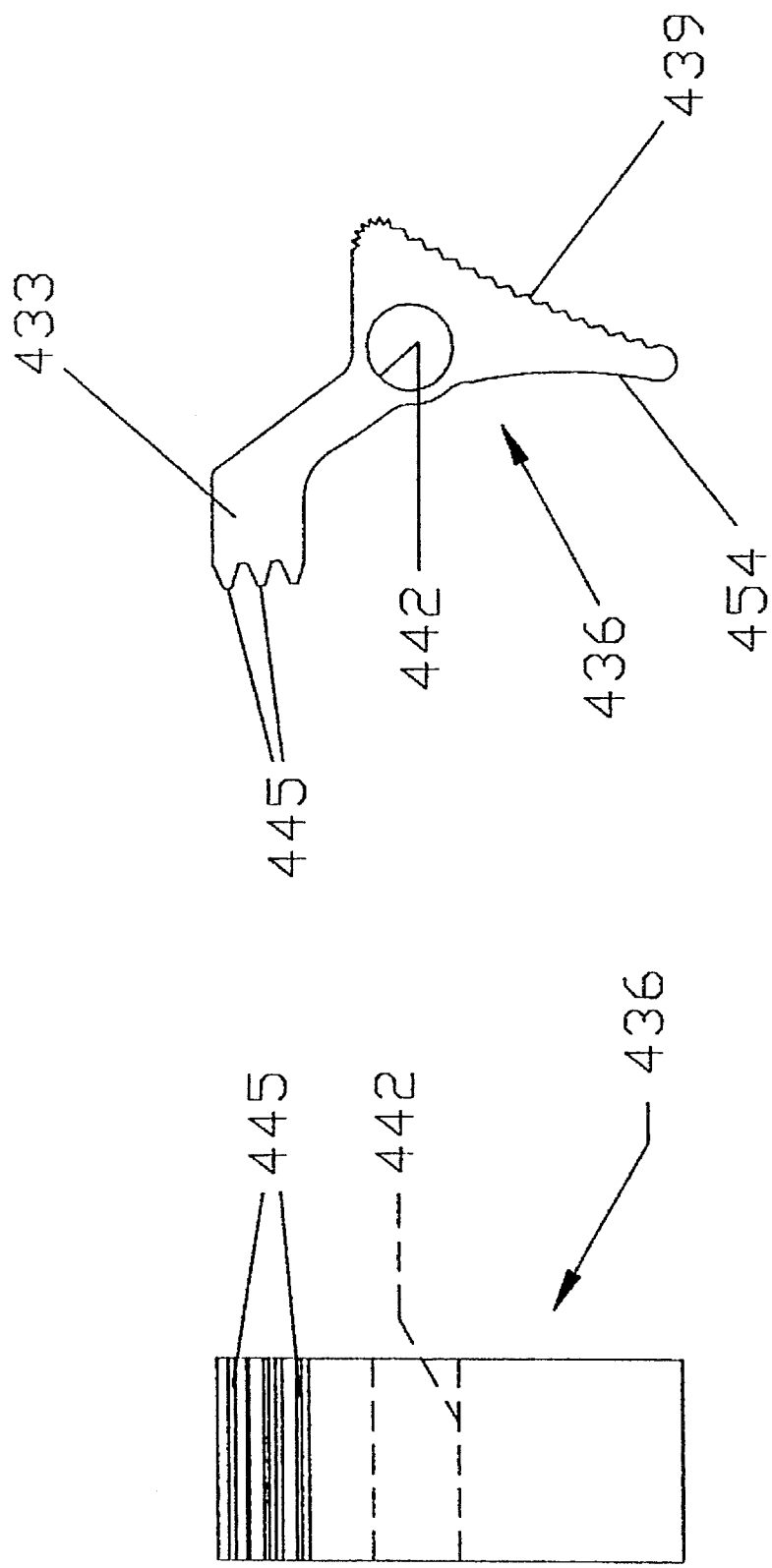

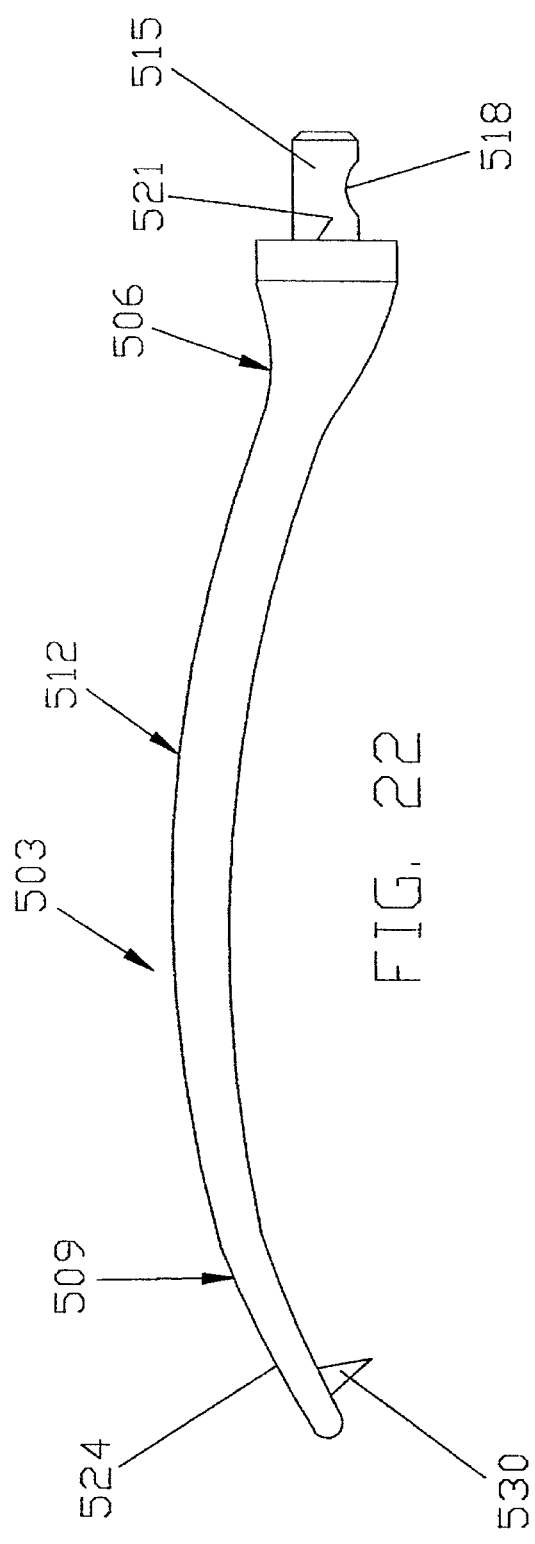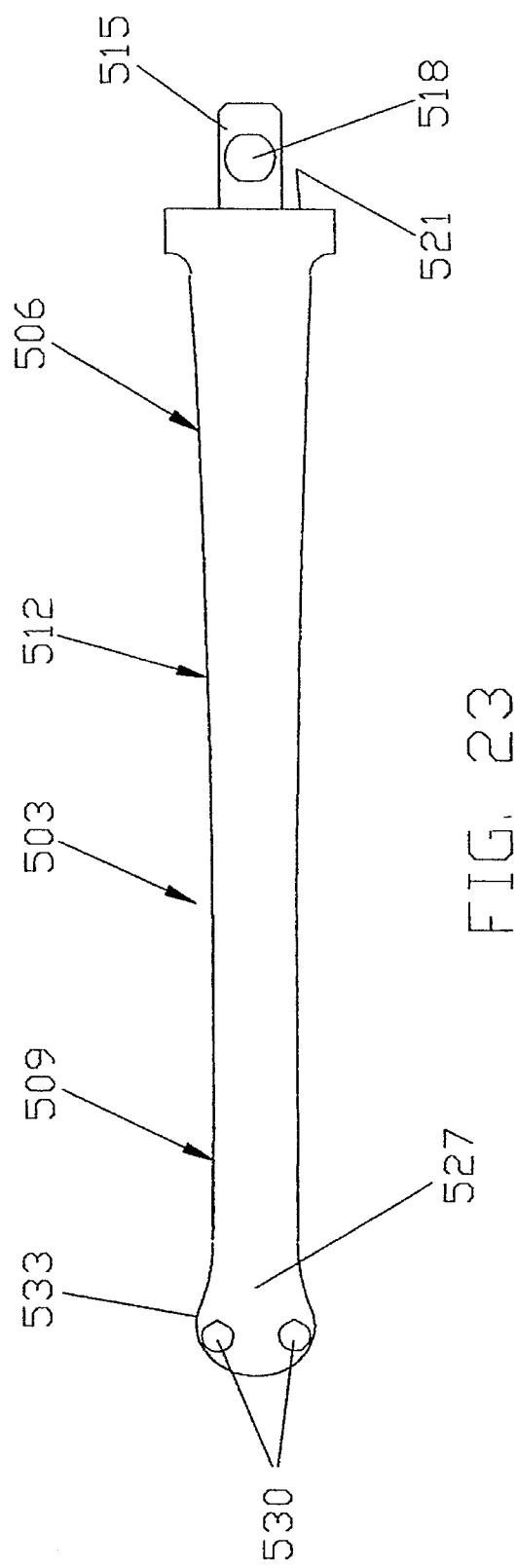

SURGICAL DRILL GUIDE

FIELD OF THE INVENTION

The present invention relates generally to surgical instruments and, more particularly, to drill guides for accurately drilling a passageway through bone.

BACKGROUND OF THE INVENTION

The anterior and posterior cruciate ligaments of the human knee cooperate, together with other ligaments and soft tissue, to provide both static and dynamic stability to the function of that joint. Often, the anterior cruciate ligament (ACL) is ruptured or torn as a result of, for example, sports related injuries. Consequently, various surgical procedures have been developed for reconstructing the ACL and restoring normal function to the knee.

In many instances, the ruptured ACL may be replaced by substituting a synthetic or harvested graft ligament in its place. More particularly, a graft ligament is attached to either the inside or outside of a tunnel formed in the surrounding bones. The graft is anchored in place by means well known in the art. Once fixed in position, the graft will cooperate with the surrounding tissue and replace the damaged ACL.

It will be appreciated that there is a complex interdependency between the ACL and the other knee ligaments, bones and soft tissue. Consequently, the precise positioning of the graft ACL relative to the surrounding bones is critical to successful reconstruction of the knee joint. In particular, the positioning and formation of the bone tunnel must be precisely controlled by the surgeon.

In U.S. Pat. No. 4,672,957 to Hourahane; U.S. Pat. No. 4,722,331 to Fox; U.S. Pat. No. 4,739,751 to Sapega et al.; U.S. Pat. No. 4,781,182 to Purnell et al.; U.S. Pat. No. 4,920,958 to Walt et al.; U.S. Pat. No. 5,112,337 to Paulos et al.; U.S. Pat. No. 5,154,720 to Trott et al.; and U.S. Pat. No. 5,163,940 to Bourque, there are disclosed a variety of drill guide means for locating a tunnel in the surrounding bones of a knee joint or the like. The foregoing patents further disclose several different methods for using these drill guides. Complete details of the construction and operation of these various drill guides and methods for their use are provided in the above-identified patents, which patents are hereby incorporated herein by reference.

It will, therefore, be understood that drill guide devices such as those taught in the above-referenced patents generally comprise a handle or other support means for holding the drill guide device exterior to the patient's body. Generally, these known drill guide devices also include a probe having a tip that is adapted to be disposed within the knee, at the point where one end of the tunnel is to exit the bone. Typically, a guide sleeve is provided for directing a guidewire or drill into position on the anterior surface of one of the bones surrounding the knee joint. The guide sleeve has its axis more or less aligned to intersect with the aforementioned probe tip and is generally slidable or variable in position relative to the support means. All of the aforementioned parts are held in relation to one another by releasable clamping or locking means known in the art.

In ACL reconstruction, these known drill guide devices are used by first placing the probe tip at or near a predetermined location on the tibial plateau. Next, the drill guide sleeve is both angularly and longitudinally adjusted relative to the probe tip so that the guide sleeve's distal end is directed toward the appropriate position on the anterior surface of the tibia. Once in place, the probe tip and drill guide sleeve are locked in position relative to each other by various means known in the art.

Prior art drill guides require various adjustments to be carried out while the surgeon is holding the device in position within the patient's body. For example, the drill guide sleeve must be released from locking engagement with the supporting member and be pushed into position with one hand, while the drill guide device is held in the surgeon's other hand. In addition, the above-referenced devices also require that the probe be locked in position by tightening a rotatable knob or other locking means. In order to make effective adjustments to the drill guide, the surgeon must observe the effects of these adjustments on the position of the probe tip within the knee. This is typically done by means of a scope or the like being positioned within the knee capsule. Unfortunately, the two-handed adjustments, required by known drill guides, often prohibit the surgeon from adequately maintaining control of the scope. In particular, the surgeon must release the scope in order to adjust the drill guide and vice-versa. This can inhibit proper positioning of the drill guide in the joint.

In any case, once the guide sleeve is adjusted and locked in position, a guidewire (K-wire) is slid through the guide sleeve and securely fastened to the tibia. The K-wire defines the tibial tunnel drilling axis. When the K-wire is seated in position on the tibia, the drill guide sleeve is unlocked and removed, longitudinally, back along the K-wire. Then the support means is removed from around the K-wire, usually by means of a side slot through which the K-wire passes. A cannulated drill is then slid over the K-wire to drill the tibial tunnel according to methods well known to those skilled in the art.

The various two-handed adjustments, required when using prior art drill guides, have significantly limited their effectiveness. Also, if the particular drill guide and probe arrangement initially chosen by the surgeon is not appropriately sized, it is necessary for the surgeon to withdraw the instrument and choose another, thus taking up valuable time during the procedure.

OBJECTS OF THE INVENTION

Accordingly, a primary object of the present invention is to provide an improved drill guide device capable of one-handed use.

Another object of the present invention is to provide a drill guide in which the guide sleeve may be discretely indexed toward the target bone surface by a one-handed operation.

A further object of the present invention is to provide a quick release locator boom, capable of being detached from the drill guide during surgery and replaced by an alternate locator boom.

Another object of the present invention is to provide for single-handed adjustment and locking/unlocking of both a locator boom housing and the guide sleeve.

A still further object of the present invention is to provide a locator boom having means for more accurately and securely positioning a probe tip on a tibial plateau.

A further object of the present invention is to provide a drill guide with means for maintaining the guide sleeve in position on the surface of the bone while a suitable guidewire is inserted and attached to the bone.

Another object of the present invention is to provide an improved method for positioning a bone tunnel during reconstructive surgery, which method includes the use of a novel drill guide that is adapted for one-handed operation.

SUMMARY OF THE INVENTION

These and other objects of the present invention are achieved through the provision and use of a novel drill guide adapted for one-handed use.

The novel drill guide of the present invention generally comprises support means having releasable locking means movably disposed thereon. Probe means are releasably mounted to the releasable locking means and disposed so that an end of the probe means may be accurately positioned within the knee capsule. Indexing means are disposed on the support means, with a cannulated drill sleeve being movably positioned therein. The cannulated drill sleeve is disposed in relation to the indexing means so that it is movable longitudinally between a first position, relative to the support means, and a plurality of discrete alternative positions, relative to the support means, in response to the actuation of the indexing means by the surgeon.

In the preferred embodiment of the present invention, the support means include a drill sleeve housing and a curved radial rack. The curved radial rack has a first portion terminating in a first end and a second portion connected to the drill sleeve housing. The curved radial rack further includes a plurality of teeth means positioned on an outer surface thereof, and angularly calibrated indicia on at least one side surface thereof.

The releasable locking means are disposed in moving engagement with the curved radial rack. The releasable locking means comprise a boom housing that is adapted for releasably engaging at least a portion of the curved radial rack's plurality of teeth means. The boom housing is movably disposed on the curved radial rack and is adjustably locked in place by means of a spring-biased locking lever that releasably engages the plurality of teeth means.

In the preferred embodiment, the probe means generally comprise a locator boom that may be releasably mounted to the boom housing or, alternatively, may be rigidly fixed thereto. The locator boom comprises a first portion and a second portion. The first portion terminates in a first end having at least one downwardly extending pointed portion. The second portion of the boom is fastened to the boom housing.

The preferred embodiment further includes a cannulated drill sleeve movably disposed within the drill sleeve housing. The cannulated drill sleeve has a proximal portion including a frusto-conical portion having a knurled or ribbed surface to provide finger grips. The cannulated drill sleeve further includes, at its distal end, bone engaging means disposed circumferentially thereabout.

The drill sleeve housing has assembled to it trigger actuated indexing means for moving the cannulated drill sleeve longitudinally between a first position, relative to the support means, and a plurality of discrete alternative positions, relative to the support means, in response to actuation of the trigger. The indexing means of the present invention comprise a thumb actuated advancing mechanism. The advancing mechanism in turn comprises spring means, gripping means, and a trigger. The spring means and gripping means are disposed within the drill sleeve housing and adapted to intermittently urge the drill sleeve distally, relative to the sleeve housing, in response to actuation of the trigger by the surgeon. The indexing means also comprise a lock/release gripper mechanism that is disposed at the proximal end of the drill sleeve housing. The lock/release gripper mechanism permits the drill sleeve to be advanced distally by the advancing mechanism with each stroke of the trigger, but prevents the drill sleeve from normally moving proximally when the trigger returns to its start position, ready for the next actuation by the surgeon.

The drill guide of the present invention may be used to accurately position a tunnel in a bone. For example, in the case of an ACL reconstruction, the first portion of the locator boom is placed inside of the target knee capsule so that the boom's downwardly extending pointed portions engage the tibial plateau at the point wherein one end of the tunnel is to exit the bone. Next, by adjusting the releasable locking means upwardly or downwardly along the curved radial rack, the surgeon may select the appropriate angular relationship between the first portion of the locator boom and the distal end of the cannulated drill sleeve. Once the releasable locking means have been locked in position on the curved radial rack, the indexing means are actuated by repeatedly pressing and releasing the trigger. This causes the cannulated drill sleeve to be advanced toward the anterior surface of the tibia. Alternatively, the drill sleeve may be advanced by simply pushing on its proximal end with the palm of the surgeon's hand. In either case, the cannulated drill sleeve is advanced under the influence of the indexing means until the bone-engaging means at the distal end of the drill guide engage the anterior surface of the tibia. A guidewire is then inserted into the drill guide and seated on the tibia. The indexing means are then released from gripping engagement with the surface of the drill sleeve, thus freeing the drill sleeve so that it may be slid away from the tibia. The drill sleeve is withdrawn back along the guidewire until it is fully removed from the site. The support means (along with the releasable locking means and probe means) are then likewise removed from the guidewire via slot means provided on one side thereof.

BRIEF DESCRIPTION OF THE DRAWINGS

These and other objects, features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 5 is a side elevational view of the cannulated drill sleeve;

FIG. 6 is a rear end view of the cannulated drill sleeve;

FIG. 7 is a front end view of the trigger showing the bifurcated thumb engaging means, drill sleeve hole and K-wire slot, and also showing the pivot axle hole in phantom;

FIG. 8 is a side elevational view of the trigger shown in FIG. 7, further illustrating a series of ribs along an upper surface of the thumb engaging means, a cam projection on a lower portion of the trigger for engaging the advancing mechanism's gripper plate, and a side view of the pivot axle hole, and further including the K-wire slot, and the drill sleeve hole in phantom;

FIG. 9 is a front end view of the advancing mechanism's single fold leaf spring;

FIG. 10 is a side elevational view of the single fold leaf spring and the gripper plate;

FIG. 13 is a front end view of the curved radial rack;

FIG. 14 is a side elevational view of the curved radial rack;

FIG. 16 is a front end view of the boom housing, with the cover removed, and further showing the locator boom mount opening;

FIG. 17 is a side elevational view of the boom housing, similar to FIG. 15 but without the locking lever being assembled therein;

FIG. 20 is a front end view of the locking lever, showing the radial rack engaging teeth, and also showing the pivot hole in phantom;

FIG. 21 is a side elevational view of the locking lever of FIG. 20, showing the thumb engaging ribs, pivot hole, and radial rack engaging teeth;

FIG. 22 is a side elevational view of the locator boom, showing the mounting projection located at the second end thereof, and one of the two downwardly extending pointed portions located at the first end thereof; and FIG. 23 is a bottom view of the locator boom, showing the aforementioned mounting projection and both of the downwardly projecting pointed portions at the first end thereof.

DETAILED DESCRIPTION OF THE PREFERRED EMBODIMENT

Figure 1:
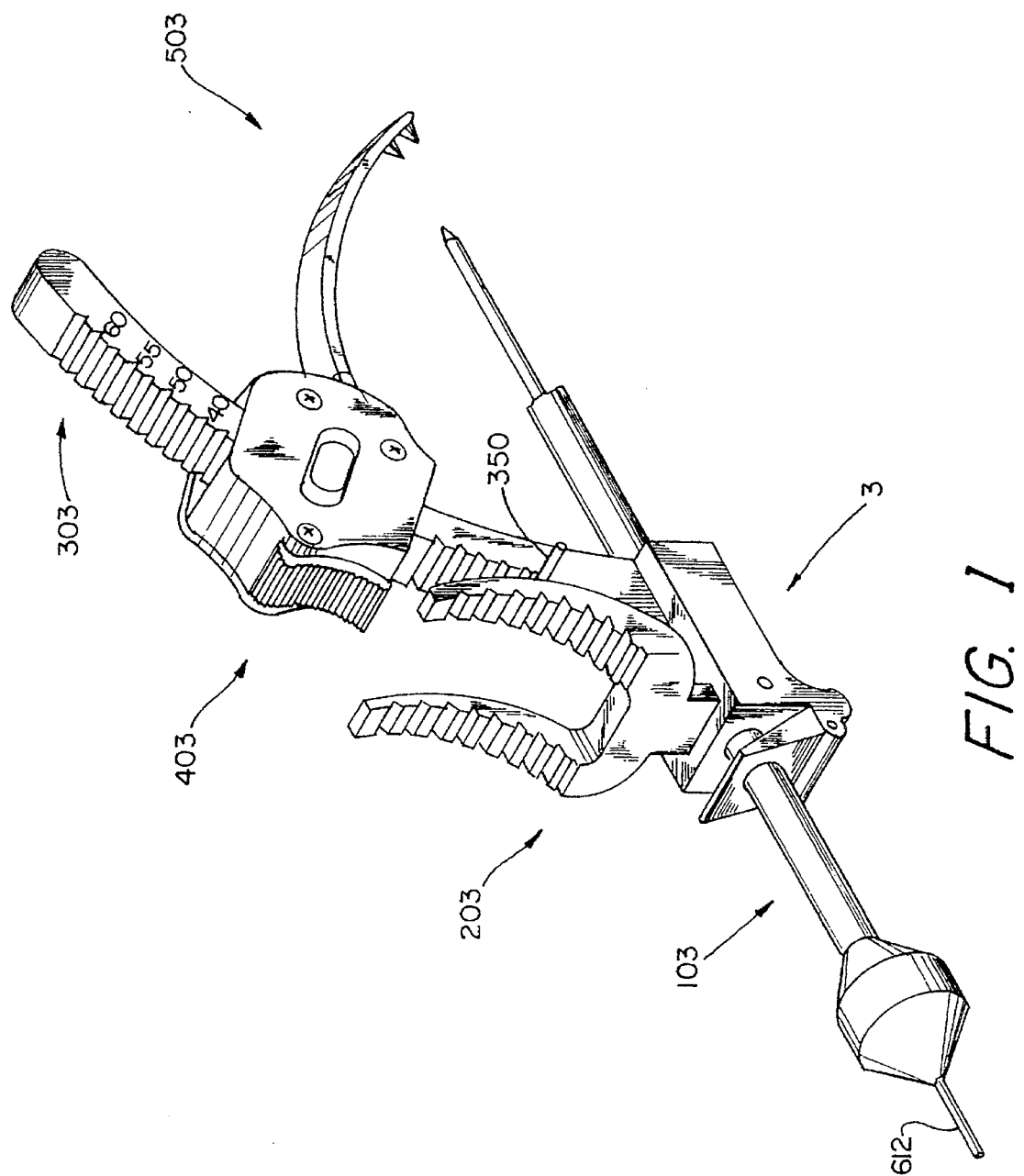
FIG. 1 is a perspective view of the drill guide of the present invention.

A perspective view of the preferred embodiment of the present invention is shown in FIG. 1. The drill guide of the present invention generally comprises a drill sleeve housing 3, a cannulated drill sleeve 103, indexing means 203, a curved radial rack 303, a boom housing 403 and a locator boom 503.

Figure 2:
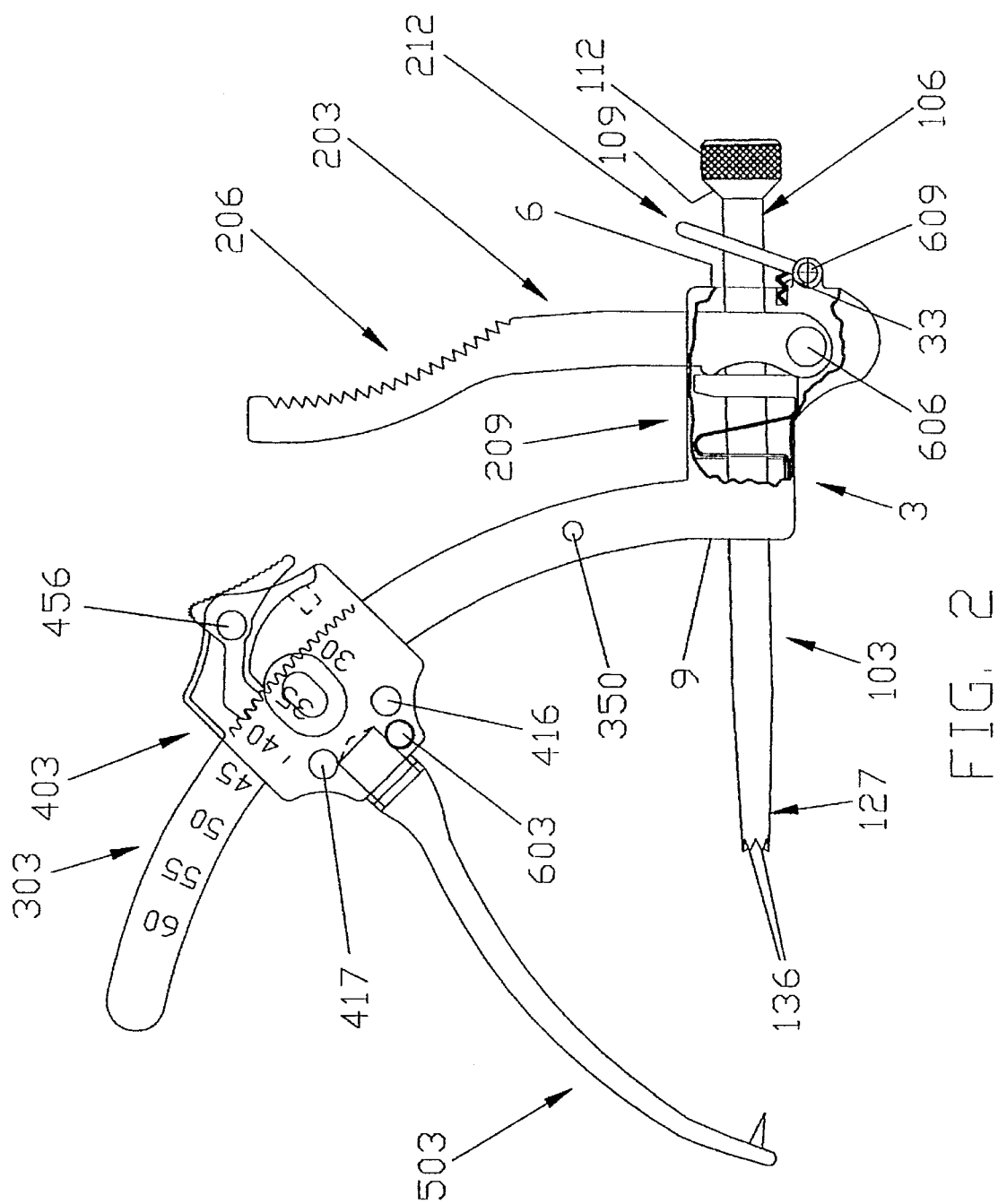
FIG. 2 is a side elevational view of the preferred embodiment of the present invention, with portions of the boom housing and the drill sleeve housing being depicted as see-through so as to aid in comprehension of the present invention.
Figure 4:
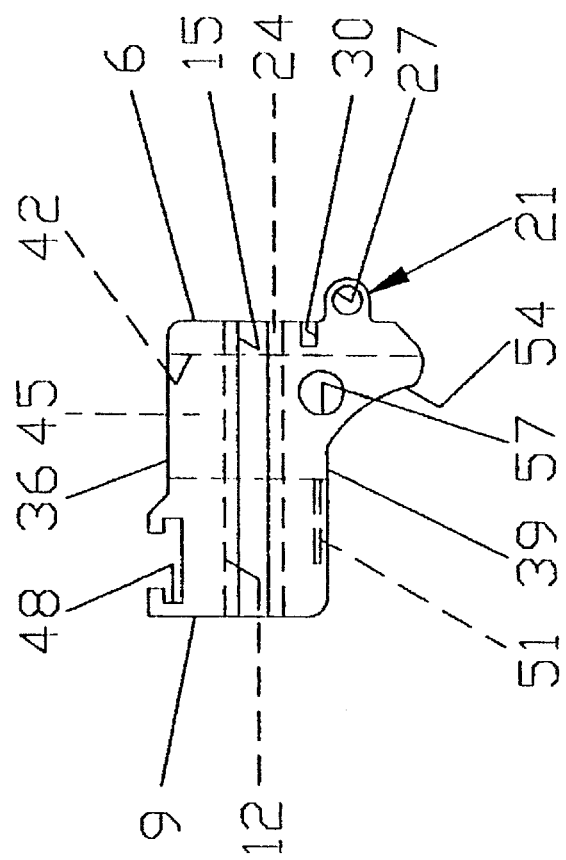
FIG. 4 is a side elevational view of the drill sleeve housing.
Figure 3:
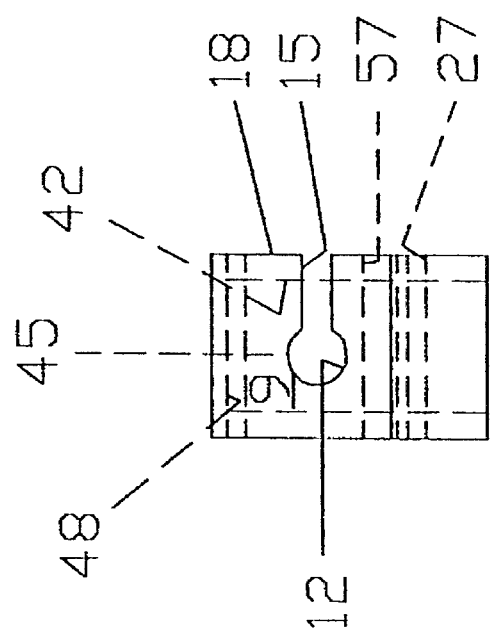
FIG. 3 is a front end view of the drill sleeve housing showing the drill sleeve bore and K-wire slot.

Referring now to FIGS. 2–4, drill sleeve housing 3 comprises a proximal end surfaced 6 and a distal end surface 9. A drill sleeve bore 12 extends the entire length of drill sleeve housing 3, from proximal end surface 6 to distal end surface 9. A slot 15 is disposed along one side of drill sleeve bore 12 and similarly extends between proximal end surface 6 and distal end surface 9. Slot 15 allows for communication between drill sleeve bore 12 and drill sleeve housing side wall 18 (FIG. 3), thus allowing for the lateral removal of a K-wire from bore 12, as will hereinafter be disclosed in further detail.

Proximal end surface 6 includes a proximally extending pivot shaft mount 21 disposed below proximal opening 24 of drill sleeve bore 12. Pivot shaft mount 21 has a central opening 27 adapted for pivotally receiving a pivot pin. A spring receiving cavity 30 (FIG. 4) is positioned above pivot shaft mount 21 and is adapted to receive a compression spring 33 (FIG. 2).

Drill sleeve housing 3 further includes a top surface 36 and a bottom surface 39. An opening 42 extends between top surface 36 and bottom surface 39 and forms an internal cavity 45. Top surface 36 also includes an inverted "T" slot 48 adapted for receiving a correspondingly-shaped portion of curved radial rack 303, as will hereinafter be disclosed in further detail. Drill sleeve housing 3 has a slot 51 disposed above bottom surface 39 and extending distally from the interior of internal cavity 45. The bottom surface 39 further includes a finger rest projection 54 extending downwardly from bottom surface 39. A trigger pivot axle opening 57 extends completely through drill sleeve housing 3. Trigger pivot axle opening 57 communicates with each side wall surface of sleeve housing 3.

Cannulated drill sleeve 103 is movably disposed within drill sleeve housing 3 as shown in FIG. 2. Cannulated drill sleeve 103 comprises a proximal portion 106 having a frusto-conical finger grip 109 as seen in FIGS. 2, 5 and 6. Finger grip 109 may have a knurled cylindrical surface 112 so as to provide for a more positive gripping during handling. Proximal portion 106 further comprises a proximal end surface 115 having a proximal bore opening 118 centrally located therein. Extending distally from frusto-conical finger grip 109 is a cannulated shaft portion 121. Cannulated shaft portion 121 is generally cylindrical and has an outer surface 124 that may be smooth or ribbed for better engagement with indexing means 203, as will hereinafter be disclosed in further detail.

Cannulated shaft portion 121 further includes a distal portion 127 having a distal end 130. Distal end 130 is circumferentially disposed about distal bore opening 133 and includes bone engaging means, such as a series of circumferentially disposed sharp projections 136 (see FIGS. 2 and 5) or a series of barbs or the like. Bone-engaging means 136 provide for a positive gripping engagement with a bone surface.

Turning now to FIG. 2, the drill guide of the present invention also comprises indexing means 203. In the preferred embodiment of the present invention, indexing means 203 in turn comprise a trigger 206, an advancing mechanism 209, and a lock-release gripper 212.

Looking now at FIGS. 2, 7 and 8, trigger 206 has an upper portion 215, a central portion 218, a lower portion 221, and proximal and distal surfaces 224 and 227, respectively.

Upper portion 215 of trigger 206 includes thumb engaging means, such as a pair of bifurcated beams 230, that extend upwardly in spaced relationship to each other from central portion 218. Bifurcated beams 230 further include a series of ribs 233 on proximal surface 224. Ribs 233 combine with a curved geometry to provide for secure receipt of the surgeon's thumb. The lower ends of bifurcated beams 230 are each fixed to one end of central portion 218. Of course, it will be understood that other configurations of the trigger's upper portion 215 may be used. For example, upper portion 215 could comprise a single beam 230 pivotally fastened to the middle of central portion 218 so as to be freely swiveled from left to right of center as needed by the surgeon.

Trigger lower portion 221 has an upper end 236 that is fixed to central portion 218 and extends downwardly therefrom to a lower end 239. Lower end 239 of lower portion 221 further includes a pivot axle receiving hole 242 disposed in substantially parallel relationship to central portion 218. A drill sleeve receiving hole 245 and K-wire slot 248 are also positioned in lower end 239 adjacent to and above pivot axle receiving hole 242 (see FIGS. 7 and 8). Lower end 239 further includes a cam projection 251 disposed on distal surface 227. Cam projection 251 is adapted for engaging advancing mechanism 209 as will hereinafter be disclosed in further detail.

In the preferred embodiment of the present invention, indexing means 203 also comprise advancing mechanism 209. Advancing mechanism 209 is shown in FIGS. 2, 9 and 10. Advancing mechanism 209 comprises a single fold leaf spring 254 and a gripper plate 257. Single fold leaf spring 254 is springingly fixed at a proximal end 260 to a corresponding edge of gripper plate 257, as seen in FIG. 10. A distally projecting portion 263 extends from a distal end 266 of single fold leaf spring 254. Portion 263 is adapted to engage slot 51 in drill sleeve housing 3 so as to fix advancing mechanism 209 within internal cavity 45 of drill sleeve housing 3.

Advancing mechanism 209 further includes a drill sleeve opening 269 centrally disposed in both single fold leaf spring 254 and gripper plate 257. Additionally, a K-wire slot 272 is disposed at one side of drill sleeve opening 269 to allow for the removal of a K-wire positioned in drill sleeve opening 269, as will hereinafter be disclosed in further detail. Gripper plate 257 further includes at least one gripping edge 275 which is located on a distal portion of drill sleeve opening 269.

Figure 12:
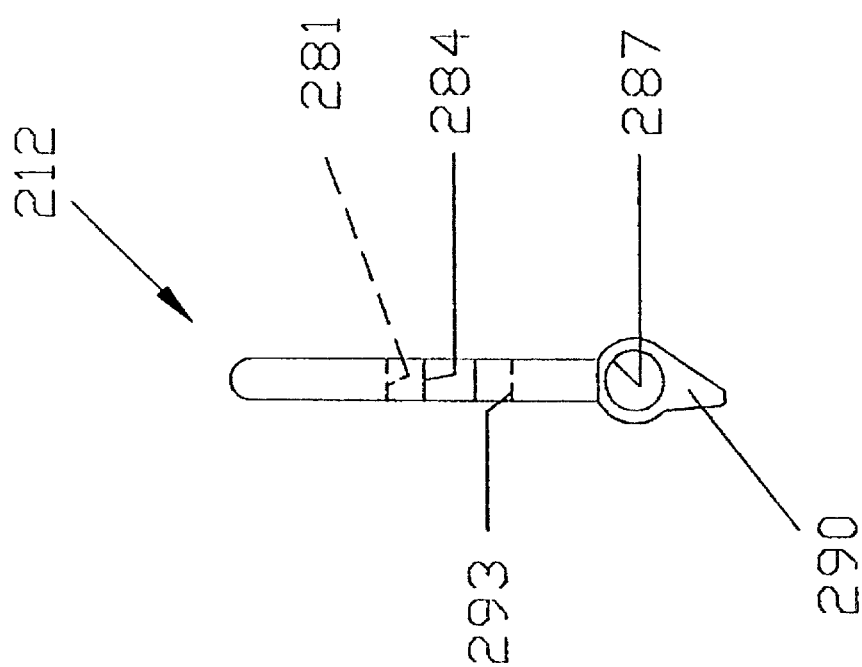
FIG. 12 is a side elevational view of the lock/release gripper showing the pivot pin hole and anti-rotation projection, and also showing the drill sleeve hole (in phantom) and the K-wire slot.
Figure 11:
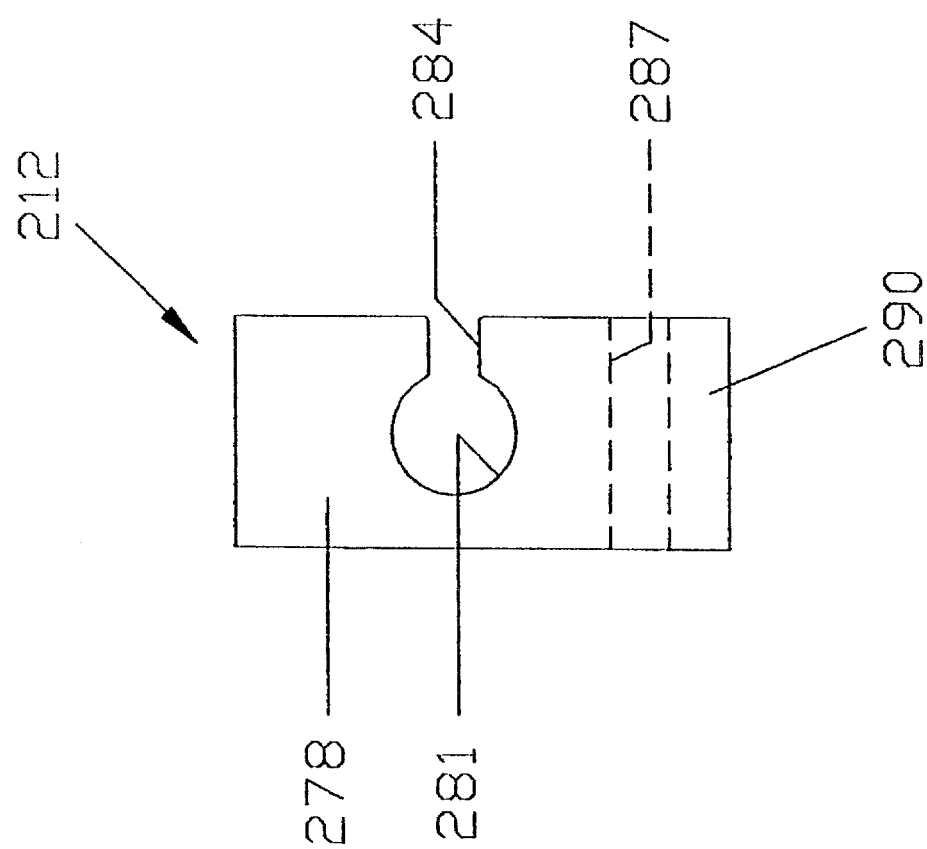
FIG. 11 is a front end view of the lock/release gripper showing a centrally positioned drill sleeve hole and K-wire slot, and also showing a pivot pin hole in phantom.

Indexing means 203 also include lock/release gripper 212. Lock/release gripper 212 is pivotally fastened to the proximally extending pivot shaft mount 21 located on proximal end surface 6 of drill sleeve housing 3 (FIG. 4). Referring now to FIGS. 2, 11 and 12, lock/release gripper 212 comprises a substantially flat plate 278 having a centrally disposed drill sleeve opening 281 and a K-wire removal slot 284. At a lower end of lock/release gripper 212 is a pivot shaft receiving bore 287 and an anti-rotation projection 290 extending downwardly therefrom. Now looking at FIGS. 2, 4, 11 and 12, compression spring 33 is disposed in the spring receiving cavity 30 which is located below drill sleeve bore 12 in sleeve housing proximal end surface 6. Lock/release gripper 212 is pivotally mounted to drill sleeve housing 3 so as to have its top end normally biased proximally by spring 33. Anti-rotation projection 290 limits the extent of rotation of gripper 212 in a clockwise direction (as seen in FIGS. 2 and 12) by engaging a lower portion of proximal end surface 6 after a predetermined rotation of lock/release gripper 212. Lock/release gripper 212 includes an edge 293 at the lower distal end of drill sleeve opening 281.

Turning now to FIGS. 2, 13 and 14, the drill guide further includes a curved radial rack 303 extending upwardly and away from the top surface 36 of drill sleeve housing 3. Curved radial rack 303 comprises a first portion 305 and a second portion 310. A curved central portion 315 extends from second portion 310 to first portion 305, thereby defining a segment of a circle as seen in FIG. 14. A series of ribs or teeth 320 are disposed on an outer surface of the rack, and angular indicia 325 are disposed on side surfaces 330 and/or 335. Angular indicia 325 allow the surgeon to mark the angular relationship between any position along the rack and second portion 310. Of course, it will be understood that curved radial rack 303 may have various cross-sections including square, rectangular, circular, etc.

Adjacent second portion 310 is a "T" shaped projection 340 adapted for mating with the inverted "T" slot 48 formed in drill sleeve housing 3 (see FIGS. 4 and 14). An opening 345 located in second portion 310 extends between side surfaces 330 and 335. A stop tab 350 (see FIGS. 1 and 2) is positioned in opening 345 to limit the travel of boom housing 403 and/or trigger 206 relative to the rack, as will hereinafter be disclosed in further detail.

Figure 15:
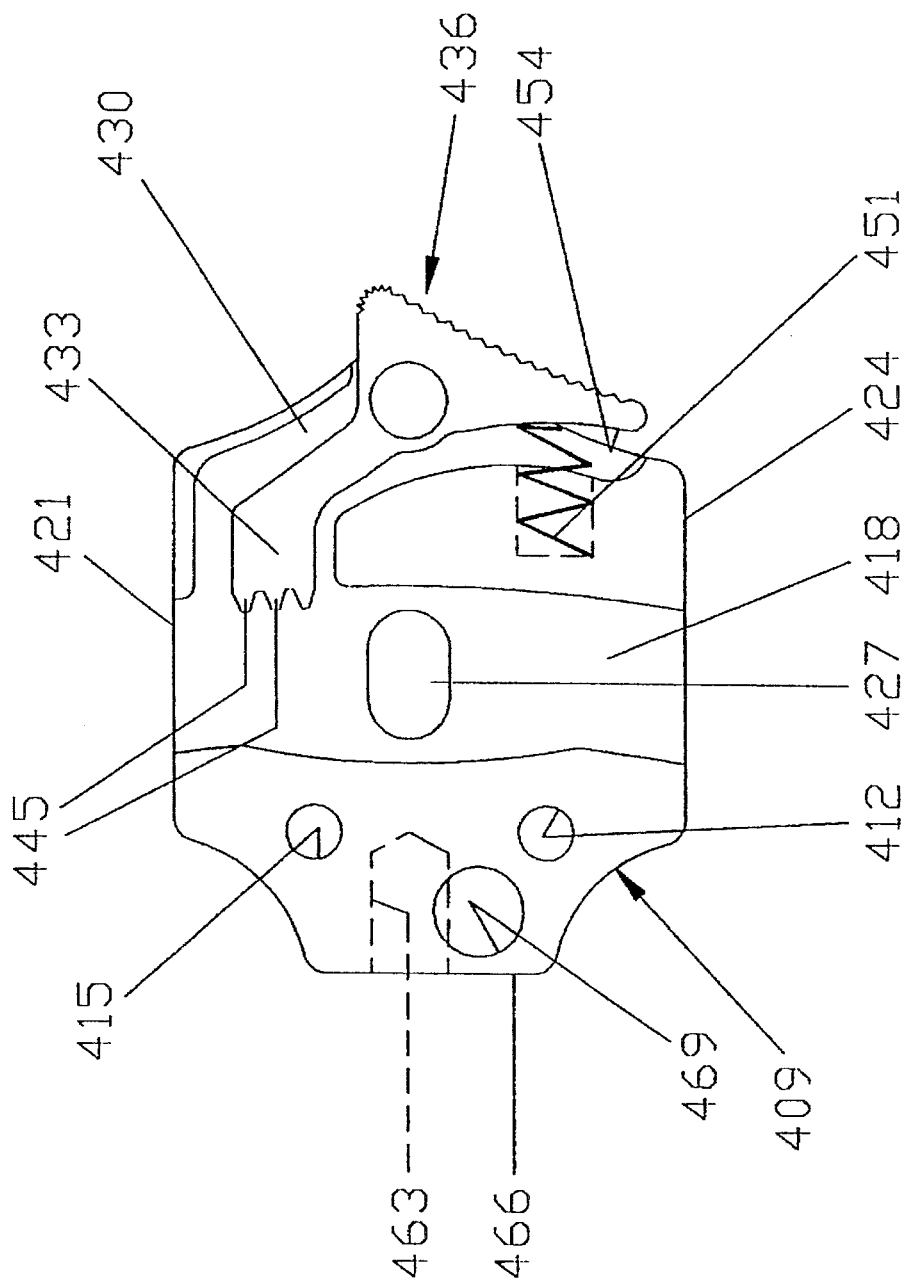
FIG. 15 is a side elevational view of the boom housing, with its cover removed, showing the locking lever pivotally positioned at one side of the housing.
Figure 19:
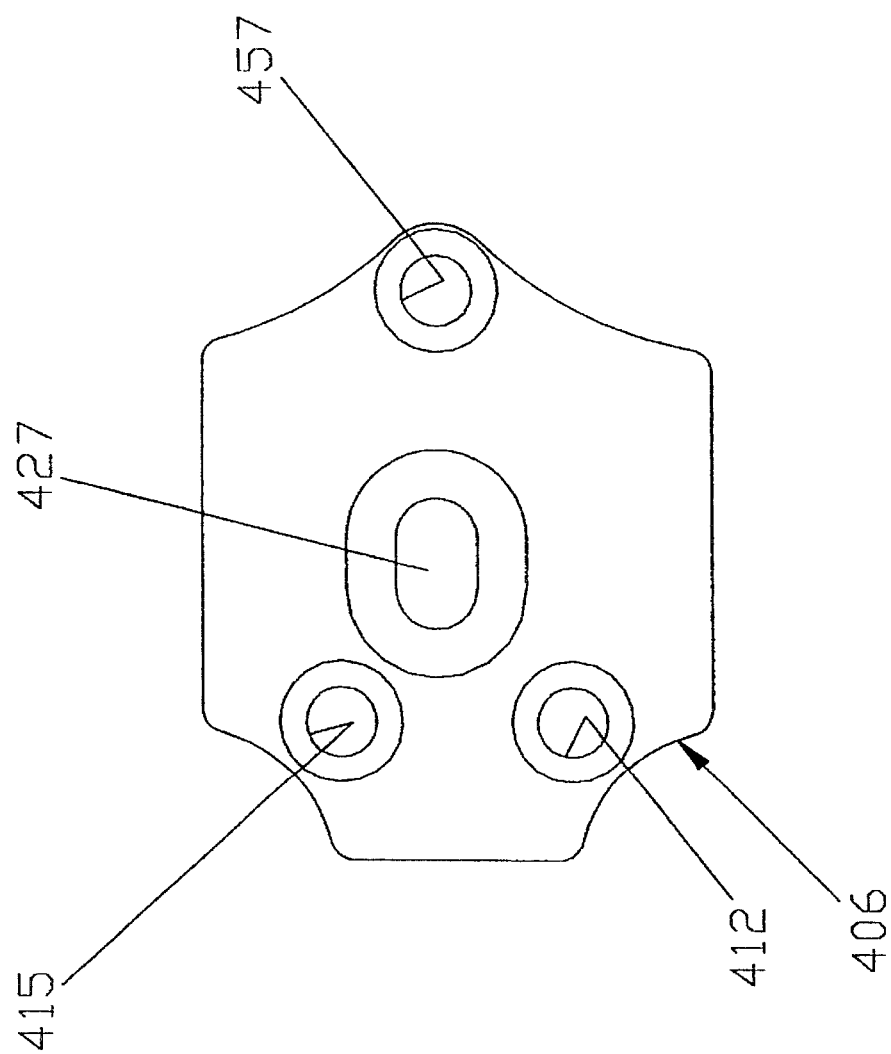
FIG. 19 is a side elevational view of the boom housing cover of FIG. 18.
Figure 18:
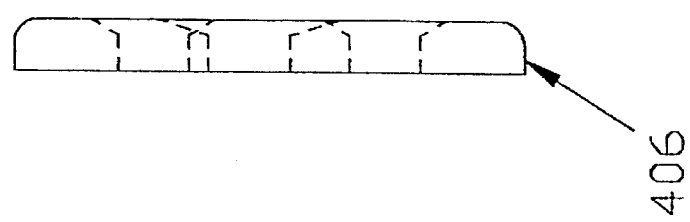
FIG. 18 is a front end view of the boom housing cover.

Referring now to FIGS. 2 and 15–21, boom housing 403 is movably disposed on curved radial rack 303. Boom housing 403 has a housing cover 406 and a housing body 409. Housing cover 406 and housing body 409 are adapted to be assembled together by fastening means well known in the art. For example, in the preferred embodiment, housing cover 406 and housing body 409 are assembled by means of screws 416 and 417 (FIG. 2) that pass through housing cover 406 and housing body 409 via holes 412 and 415 respectively, as well as a pin 456 (FIG. 2) passing through cover hole 457 (FIG. 19) and body hole 460 (FIG. 17), as will hereinafter be described in further detail. Housing body 409 further includes a central passageway 418 that communicates between top surface 421 and bottom surface 424 (see FIG. 15). Central passageway 418 is sized so as to allow boom housing 403 to freely and movingly engage curved radial rack 303. A window 427 is centrally disposed in housing body 409 and/or cover 406 so as to open into central passageway 418. Thus, window 427 provides a viewing port for viewing angular indicia 325 on curved radial rack 303 when boom housing 403 is disposed on curved radial rack 303. Central passageway 418 further communicates with an opening 430, thus providing access for the engaging portion 433 of a releasable locking lever 436 to enter central passageway 418, as seen in FIG. 15.

Looking now at FIGS. 20 and 21, releasable locking lever 436 includes a ribbed thumb engaging portion 439, a hole 442, and the aforementioned radial rack engaging portion 433. Radial rack engaging portion 433 further includes a plurality of teeth 445 adapted for engaging teeth 320 on the outer surface of curved radial rack 303.

Referring again to FIGS. 15 and 17, boom housing body 409 further comprises a cavity 448 adapted for receiving compression spring 451. Compression spring 451 is disposed in cavity 448 so as to engage release lever 436 on its bottom surface 454. Thus, locking lever 436 is normally pivotally biased by compression spring 451 so as to have its plurality of teeth 445 project out of proximal opening 430 into central passageway 318. Locking lever 436 is pivotally assembled to boom housing 403 by a pin 456 (FIG. 2) which is inserted through opening 457 in cover 406 and opening 460 in boom housing body 409 (see FIGS. 2, 17 and 19).

Boom housing body 409 further includes a mounting hole 463 located between screw holes 412 and 415 and opening outwardly from surface 466, as seen in FIGS. 15, 16, and 17. A releasable locking pin receiving hole 469 may be positioned adjacent to and slightly intersecting a portion of mounting hole 463 if locator boom 503 is to be releasable from boom housing body 409. Mounting hole 463 is adapted to receive a corresponding mounting feature on locator boom 503, as will hereinafter be disclosed in further detail.

Looking now at FIGS. 2, 22 and 23, locator boom 503 comprises a first portion 509, a second portion 506, and a curved central portion 512 extending between first portion 509 and second portion 506. Second portion 506 further includes a mounting projection 515 and may include a locking pin receiving detent 518 disposed on at least one surface thereof.

Locator boom 503 is adapted for insertion into the mounting hole 463 formed in boom housing 403. More particularly, mounting projection 515 is inserted into mounting hole 463 until the locator boom's shoulder 521 contacts the boom housing's corresponding surface 466 (see FIGS. 2, 15, 16, 17, 22 and 23). Once shoulder 521 has contacted the corresponding surface 466, a locking pin 603 (FIG. 2) is inserted through the boom housing's locking pin receiving hole 469 so as to engage detent 518, thereby fastening locator boom 503 in position in boom housing 403. At the same time, it will be appreciated that detent 518 also acts as an orientation pilot feature so as to ensure proper orientation of locator boom 503 in boom housing 403. Preferably locking pin 603 is easily removable, so as to permit the locator boom 503 to be detached from boom housing 403 if and when desired. Alternatively, locator boom 503 may be permanently attached to boom housing 403 in ways well known in the art.

Looking again at FIGS. 22 and 23, boom first portion 509 includes a top surface 524 and a bottom surface 527. Extending downwardly from bottom surface 527 is at least one and, preferably, a pair of pointed projections 530. Pointed projections 530 are adapted for securely engaging a predetermined point on a bone surface where a bone tunnel is to exit. As seen in FIG. 23, first portion 509 further comprises a paddle shaped portion 533 from which pointed projections 530 extend downwardly. Thus first portion 509 of locator boom 503 generally resembles a "cobra's head". Of course, it will be understood that locator boom 503 may be formed with various alternate cross-sections and/or shapes if desired.

Looking now at FIGS. 1 and 2, the preferred embodiment of the present invention is assembled in the following manner. First, a locator boom 503 is releasably locked into position in boom housing 403. More particularly, the locator boom's mounting projection 515 (see FIGS. 22 and 23) is inserted into the boom housing's mounting hole 463 so that detent 518 is aligned with locking pin receiving hole 469 (see FIGS. 15 and 17). At this point, the locator boom's shoulder 521, is pushed into contact with the boom housing's surface 466. Once in place, a locking pin 603 (see FIG. 2) is inserted in hole 469 and passed therethrough, thus engaging detent 518 and locking the locator boom 503 to boom housing 403.

Next, curved radial rack 303 is assembled to drill sleeve housing 3 by inserting the rack's "T" shaped projection 340 (see FIG. 14) into the housing's inverted "T" slot 48 (see FIG. 4) so that curved radial rack 303 extends upwardly and away from drill sleeve housing 3 (see FIGS. 1 and 2). Curved radial rack 303 may be either releasably or permanently fixed to drill sleeve housing 3 in this manner. Alternatively, curved radial rack 303 may be either releasably or permanently fixed to drill sleeve housing 3 in some other manner of the sort well known in the art. Boom housing 403 is then slid into position along curved radial rack 303. More particularly, first portion 305 of curved radial rack 303 (see FIG. 14) is inserted into central passageway 418 of boom housing body 409 (see FIGS. 15 and 17). Central passageway 418 is adapted to allow curved radial rack 303 to freely slide therethrough. Curved radial rack 303 is oriented within central passageway 418 so that teeth 320 (see FIG. 14) of curved radial rack 303 will come into contacting engagement with the plurality of teeth 445 at engaging portion 433 of locking lever 436 (see FIGS. 15, 20 and 21). Boom housing 403 is limited in its downward travel along curved radial rack 303 by stop tab 350 (see FIG. 2).

Advancing mechanism 209 is assembled to drill sleeve housing 3 by inserting it through the bottom end of the opening 42 which is formed in drill sleeve housing 3 (see FIGS. 3 and 4). More particularly, advancing mechanism 209 is first slightly compressed between the thumb and forefinger of the assembler, and then it is inserted through the bottom end of opening 42 until the advancing mechanism is fully located within internal cavity 45. Advancing mechanism 209 is oriented such that its K-wire slot 272 (see FIGS. 9 and 10) aligns with K-wire slot 15 (see FIGS. 3 and 4) of drill sleeve housing 3.

Once in position in internal cavity 45, advancing mechanism 209 is allowed to spring back toward its normally unstressed position, thus driving its mounting projection 263 (see FIGS. 9 and 10) into slot 51 in drill sleeve housing 3 (see FIG. 4). Thus, advancing mechanism 209 is locked within the drill sleeve housing's internal cavity 45 (see FIG. 2). Trigger 206 (see FIGS. 7 and 8) is then inserted through the top end of the opening 42 which is formed in drill sleeve housing 3, until the trigger's pivot axle receiving hole 242 (see FIGS. 7 and 8) is aligned with the drill sleeve housing's pivot axle opening 57 (see FIGS. 3 and 4). At this point, an axle 606 (see FIG. 2) is inserted through the drill sleeve housing's pivot axle opening 57 and the trigger's pivot axle receiving hole 242, thus pivotally fastening trigger 206 to drill sleeve housing 3. In this configuration, camming projection 251 (see FIG. 7) engages the proximal side of gripper plate 257. Thus, single fold leaf spring 254 urges gripper plate 257 against cam projection 251 and thereby biases trigger 206 in a clockwise direction so that the proximal side of the trigger rests against the drill sleeve housing.

Lock/release gripper 212 is then pivotally attached to drill sleeve housing 3. This is done by positioning a compression spring 33 in the drill sleeve housing's cavity 30 (see FIG. 2), then aligning the pivot shaft receiving bore 287 (see FIGS. 11 and 12) of the lock/release gripper 212 with the central opening 27 of pivot shaft mount 21 (see FIG. 4), and then rotatably pinning lock/release gripper 212 to drill sleeve housing 3 with a pivot pin 609 (see FIG. 2).

Next, cannulated drill sleeve 103 is positioned in drill sleeve housing 3, as seen in FIGS. 1 and 2. More particularly, distal portion 127 of drill sleeve 103 (see FIG. 5) is passed through lock/release gripper central hole 281 (see FIGS. 11 and 12) and into the drill sleeve bore 12 of drill sleeve housing 3. During this insertion of drill sleeve 103, lock/release gripper 212 is rotated counterclockwise toward proximal surface 6 of sleeve housing 3. This action disengages hole edge 293 (see FIG. 12) from engagement with the drill sleeve's outer surface 124. Once disengaged from edge 293, drill sleeve 103 slides freely into sleeve housing 3. Sleeve distal portion 127 extends through opening 245 of trigger 206 (see FIGS. 7 and 8), through hole 269 in advancing mechanism 209 and exits the distal side of drill sleeve housing 3 (see FIGS. 1 and 2).

The surgical drill guide of the present invention is used as follows. First, the surgeon slides boom housing 403 (see FIG. 2) along curved radial rack 303 until the surgeon sees the correct angular indicia 325 (see FIG. 14) through window 427 (see FIG. 19). More particularly, the surgeon presses ribbed thumb engaging portion 439 of locking lever 436, thus compressing spring 451 and pivoting locking lever 436 clockwise (see FIG. 15). As locking lever 436 pivots, its teeth 445 disengage from the teeth 320 of curved radial rack 303 (see FIG. 14), thus freeing boom housing 403 to slide on the curved radial rack 303 with a convenient thumb motion. The surgeon then manually slides boom housing 403 upwardly or downwardly along curved radial rack 303. Boom housing 403 is limited in its downward travel along curved radial rack 303 by stop tab 350 (see FIGS. 1 and 2).

It will be understood that the adjustment of boom housing 403 can be done while the surgeon is holding the drill guide in one hand and without the necessity of any second hand adjustment. More particularly, the surgeon places his or her index finger on boom housing 403, while at the same time placing his or her ring and middle fingers against rack 303 and/or drill sleeve housing 3, below boom housing 403. The surgeon then places his or her little finger on the drill sleeve housing's finger rest projection 54, and positions his or her thumb on ribbed thumb engaging portion 439 of locking lever 436. The surgeon then depresses locking lever 436 and urges boom housing 403 into the desired position using his or her thumb. Boom housing 403 is locked on curved radial rack 303 by releasing locking lever 436 and thus engaging the lever's teeth 445 with rack teeth 320.

The surgeon then positions the boom's pointed portions 530 at the location on the bone where the tunnel is to exit. Next, the surgeon indexes drill sleeve 103 into position against the anterior surface of the bone by depressing trigger 206 with his or her thumb. It will be appreciated that this can be conveniently accomplished, simply by moving his or her thumb off locking lever 375 and onto the adjacent trigger 206. More particularly, depressing trigger 206 causes its cam portion 251 to engage the proximal side of gripper plate 257 (see FIGS. 2, 8 and 10). Cam portion 251 forces gripper plate 257 to springingly pivot about the proximal end 260 of leaf spring 254, while at the same time compressing single fold leaf spring 254. This action, in turn, causes the gripper plate's edge 275 (see FIG. 10) to engage the outer surface 124 of drill sleeve 103. As single fold leaf spring 254 is compressed within internal cavity 45, drill sleeve 103 is slid distally, relative to drill sleeve housing 3, by a predetermined distance. This predetermined distance is determined by the longitudinal travel of gripper plate 257 within drill sleeve housing 3, once the gripper plate's edge 275 has engaged the outer surface 124 of drill sleeve 103. It is to be noted that lock/release gripper 212 does not impede distal movement of drill sleeve 103 during this indexing movement, since any initial binding which may occur between the lock/release gripper's edge 293 and the outer surface 124 of drill sleeve 103 will be released as soon as lock/release gripper 212 begins to pivot counterclockwise with the advancing drill sleeve.

Upon releasing pressure from trigger 206, leaf spring 254 urges gripper plate 257 proximally, disengaging edge 275 from the drill sleeve. As this occurs, lock/release gripper 212 is biased proximally with respect to drill sleeve housing 3, by compression spring 33 (see FIG. 2). This causes edge 293 of lock/release gripper 212 to engage the outer surface 124 of drill sleeve 103. Thus drill sleeve 103 is locked in position against proximal movement by lock/release gripper 212 while advancing mechanism 209 returns to its normal position. Once trigger 206 returns to its normal position, the surgeon may once again depress trigger 206 and thereby advance drill sleeve 103 distally by another incremental distance.

Of course, it will be appreciated that a surgeon may also manually slide cannulated drill sleeve 103 distally within sleeve housing 3 simply by pressing on the sleeve's proximal end surface 115 with the palm of his or her hand. This causes drill sleeve 103 to slide freely through the pivoting lock/release gripper 212 and drill sleeve housing 3 and into position against the anterior surface of the bone, as discussed above.

It should also be noted that in order to pull drill sleeve 103 proximally from drill sleeve housing 3, the surgeon must first release edge 293 of lock/release gripper 212 from engagement with drill sleeve 103. This may be accomplished by manually rotating lock/release gripper 212 in a counterclockwise direction so as to compress spring 33. This in turn releases edge 293 from engagement with the sleeve's outer surface 124, thus freeing drill sleeve 103 to move proximally with respect to sleeve housing 3.

As distal portion 127 of drill sleeve 103 approaches the anterior surface of the bone, bone engaging means 136 engage the bone surface, thus retaining the cannulated drill sleeve in position. Once in this position, the drill guide is automatically locked in place without any further activity by the surgeon, since locking lever 436 will hold locator boom 503 in position and lock/release gripper 212 will hold drill sleeve 103 in position. The surgeon may then insert a K-wire 612 (see FIG. 1) through cannulated drill sleeve 103 and fasten it to the correct position on the target bone.

Once the K-wire is securely fastened to the bone, drill sleeve 103 is slid out along the K-wire and removed. More particularly, the surgeon depresses lock/release gripper 212, thus compressing spring 33 and disengaging the gripper's edge 293 from contact with the drill sleeve's outer surface 124. Once edge 293 is no longer contacting drill sleeve surface 124, the surgeon may grip the drill sleeve's frusto-conical finger grip 109 by means of the knurled surface 112 and draw the cannulated drill sleeve from the sleeve housing and back along the K-wire until the drill sleeve is altogether removed.

Once cannulated drill sleeve 103 has been removed from the K-wire, the drill guide is removed from the K-wire and withdrawn from the patient's body. More particularly, the surgeon depresses the boom housing's locking lever 436, thereby compressing spring 451 and disengaging the lever's teeth 445 from the curved rack's teeth 320. Boom housing 403 is then slid along curved radial rack 303 until the boom's pointed portions 530 and its first portion 509 can be disengaged from the bone. Then the K-wire is slid through slots 272, 248 and 284 of indexing means 203, and through slot 15 in drill sleeve housing 3, thus freeing the drill guide from the K-wire and allowing for its removal from the patient's body.

It is to be appreciated that numerous changes may be made to the preferred embodiment described above without departing from the scope of the present invention.

Thus, for example, locator boom 503 might be formed with three projecting portions 530.

Furthermore, in those circumstances where it is sufficient for the cannulated drill sleeve 103 to be manually advanced by the surgeon simply by pressing on the proximal end of the drill sleeve with the palm of his or her hand, selected portions of indexing means 203 may be omitted entirely from the apparatus. In particular, in this case, trigger 206, single fold leaf spring 254 and gripper plate 257 may be omitted entirely, and the indexing means 203 can be formed using only the lock/release gripper 212.

It should also be appreciated that alternative means might be used to connect boom housing 403 to curved radial rack 303. What is important is that the alternative means mechanically secure boom housing 403 to curved radial rack 303 and permit it to be intentionally and directly moved relative to the rack using a single-handed operation.

Furthermore, alternative apparatus might be used to index drill sleeve 103 forward relative to drill sleeve housing 3. By way of example, trigger 206, single fold leaf spring 254 and gripper plate 257 might be replaced by a rack and pinion assembly or by a ratchet-type assembly. In such a situation, lock/release gripper 212 might be retained, or it might be replaced by a detent-type assembly of the sort well known in the art. Again, what is important is that the alternative indexing means permit drill sleeve 103 to be movably connected to drill sleeve housing 3 so that the drill sleeve can be intentionally and directly moved forward relative to housing 3 using a single-handed operation.

These and other changes of their type are considered to be within the scope of the present invention.

What is claimed is:

1. A device for guiding and positioning surgical instruments, used when forming a passageway in bone, said device comprising, in combination:

a support housing;

releasable locking means moveably assembled to said support housing for one-handed positioning of a locator boom mounted on said releasable locking means, said locator boom comprising a beam extending outwardly from said releasable locking means and toward said bone;

a cannulated drill sleeve moveably mounted to said support housing; and indexing means assembled to said support housing and having said cannulated drill sleeve releasably engaged therewith, said indexing means being adapted to permit said cannulated drill sleeve to be moved between a first position, relative to said support housing, and a plurality of alternative positions, relative to said support housing, in response to a one-handed actuation of said indexing means, and further wherein said indexing means are adapted to permit said cannulated drill sleeve to be advanced distally by pressing on said proximal end of said cannulated drill sleeve and said cannulated drill sleeve to be withdrawn proximally by manually actuating selected portions of said indexing means.

2. A device according to claim 1 wherein said locator boom comprises a bone engaging end that is spaced away from said releasable locking means and includes an upper surface and a lower surface, said bone engaging end lower surface including at least one downwardly extending pointed portion.

3. A device according to claim 2 wherein said locator boom has a paddle shaped bone engaging end.

4. A device according to claim 1 wherein said locator boom is fixedly mounted to said releasable locking means.

5. A device according to claim 1 wherein said support housing comprises a plurality of external surfaces, an internal cavity that is accessible from at least one of said surfaces, and a bore passing therethrough, said bore being adapted to receive said cannulated drill sleeve, and further wherein said support housing comprises an upwardly extending curved radial adapted to slidingly support said releasable locking means, said curved radial rack including a first portion terminating in a first end and a second portion spaced away from said first end comprising mounting means for mounting said curved radial rack to one of said external surfaces of said support housing.

6. A device according to claim 5 wherein said curved radial rack is releasably mounted on said one of said external surfaces of said support housing.

7. A device according to claim 5 wherein said curved radial rack defines a segment of a circle.

8. A device according to claim 5 wherein said curved radial rack comprises angular indicia on at least one side surface thereof.

9. A device according to claim 8 wherein said releasable locking means comprise a locator boom housing adapted for selectively engaging said curved radial rack and further including a thumb actuated locking lever that is pivotally biased to said locator boom housing so as to provide for a one-handed position adjustment of said locator boom housing upwardly or downwardly along said curved radial rack, said locking lever includes a rack engaging portion arranged so as to be in normally locking engagement with said curved radial rack.

10. A device according to claim 9 wherein said rack engaging portion of said locking lever includes a plurality of teeth adapted for engaging a corresponding plurality of teeth disposed on a rear surface of said curved radial rack.

11. A device according to claim 9 wherein said locator boom housing includes an opening disposed in a side wall thereof so as to provide a window for viewing said angular indicia.

12. A device according to claim 9 wherein said curved radial rack further comprises a stop disposed at said second portion thereof so as to limit the downward travel of said locator boom housing along said curved radial rack.

13. A device according to claim 1 wherein said support housing includes a plurality of external surfaces, an internal cavity that is accessible from at least one of said surfaces, and a bore passing therethrough, said bore being adapted to receive said cannulated drill sleeve, and further wherein said indexing means comprise an advancing mechanism that is positioned within said internal cavity comprising a leaf spring having one end fixed to said support housing and another end flexibly fastened to a gripper plate, wherein said leaf spring and said gripper plate include a central bore sized so as to slidingly receive said cannulated drill sleeve, a trigger that is biased by said leaf spring whereby when said trigger is actuated, said gripper plate grips said cannulated drill sleeve so as to move said cannulated drill sleeve from said first position to said plurality of alternative positions, and a lock/release gripper plate pivotally fastened to an external end surface of said support housing, said lock/release gripper plate including a central bore and being spring biased outwardly relative to said external surface so as to grip said cannulated drill sleeve when said trigger is released.

14. A device according to claim 13 wherein said trigger includes a lower portion that is pivotally mounted within said internal cavity of said support housing and positioned relative to said advancing gripper plate so as to engage said advancing gripper plate along one side thereof and thereby compress said leaf spring each time said trigger is actuated.

15. A device according to claim 14 wherein said trigger comprises at least a pair of thumb engaging portions extending upwardly relative to said housing and disposed so as to straddle a curved radial rack that is mounted to said external surface of said housing.

16. A device according to claim 14 wherein said trigger further comprises an upper portion that is pivotally fastened to said lower portion so as to allow said upper portion to be swiveled from side to side relative to said lower portion.

17. A device according to claim 14 wherein said trigger comprises a single portion extending upwardly relative to said housing.

18. A device according to claim 13 wherein each of said advancing mechanism, said trigger and said lock/release gripper plate further comprise a side slot adapted for removing a guidewire.

19. A device according to claim 1 wherein said support housing includes a plurality of external surfaces, an internal cavity that is accessible from at least one of said surfaces, and a bore passing through said support housing, said bore being adapted for receiving said cannulated drill sleeve, and further wherein said indexing means comprise a lock/release gripper plate pivotally fastened to an external end surface of said support housing, said lock/release gripper plate being spring biased outwardly relative to said external end surface so as to (i) normally grip said cannulated drill sleeve with an edge defined by a centrally positioned bore so as to prohibit said cannulated drill sleeve from moving in a proximal direction until said lock/release gripper plate is moved inwardly relative to said external end surface, yet (ii) slidably release said cannulated drill sleeve when said lock/release gripper plate is urged toward said external end surface and thereby permit said cannulated drill sleeve to be moved in a distal direction.

20. A device according to claim 1 wherein said indexing means comprise a lock/release gripper plate pivotally fastened to an external end surface of said support housing, said lock/release gripper. plate being spring biased outwardly relative to said external end surface so as to fi) normally grip said cannulated drill sleeve with an edge defined by a centrally positioned bore yet (ii) slidably release said cannulated drill sleeve when said lock/release gripper plate is single-handedly urged toward said external end surface, thereby permitting said cannulated drill sleeve to be advanced toward a target bone by pushing it through said support housing with one hand.

21. A device according to claim 1 wherein said cannulated drill sleeve includes bone-engaging means for gripping a bone surface, said means being disposed at a distal end of said cannulated drill sleeve.

22. A device for guiding and positioning surgical instruments, used when forming a passageway in bone, said device comprising, in combination:

a support comprising a housing and a curved radial rack extending upwardly and away from said housing, said curved radial rack including a first portion terminating in a first end and a second portion spaced away from said first end comprising mounting means for mounting said curved radial rack to an end of said housing, said curved radial rack further including a plurality of teeth positioned on an outer surface thereof;

releasable locking means moveably assembled to said curved radial rack for one-handed positioning of a locator boom relative to a target bone, said releasable locking means including a lever having a portion thereof adapted to releasably engage at least a portion of said plurality of teeth so as to hold said releasable locking means at a fixed position along said curved radial rack, and said locator boom comprising a curved beam extending outwardly from said releasable locking means and toward said bone and including a first portion and a second portion, said second portion of said locator boom being releasably mounted to said releasable locking means, and said first portion terminating in a first end having at least one downwardly extending pointed portion;

a cannulated drill sleeve moveably disposed within a central bore of said housing; and said housing further comprising trigger actuated indexing means positioned within an internal cavity of said housing for moving said cannulated drill sleeve longitudinally through said central bore between a first position, relative to said support, and a plurality of other discrete positions, relative to said support, said indexing means comprising (i) an advancing mechanism positioned within said internal cavity comprising a leaf spring having one end fixed to said housing and another end flexibly fastened to a gripper plate wherein said leaf spring and said gripper plate include a central bore sized so as to slidingly receive said cannulated drill sleeve, (ii) a trigger that is biased by said leaf spring whereby when said trigger is actuated, said gripper plate grips said cannulated drill sleeve so as to move said cannulated drill sleeve from said first position to said plurality of other discrete positions, and (iii) a lock/release gripper plate pivotally fastened to an external end surface of said housing, said lock/release gripper plate including a central bore and a spring positioned between said external end surface and said lock/release gripper plate so as to bias said lock/release gripper plate outwardly relative to said external surface of said housing thus gripping said cannulated drill sleeve when said trigger is released.

23. A method for positioning a passageway in a bone, said method comprising the steps of:

(1) providing a device for guiding and positioning a guidewire or drill to a point on a first bone surface where a tunnel is to begin, said device comprising, in combination:

a support housing;

releasable locking means moveably assembled to said support housing for one-handed positioning of a locator boom mounted on said releasable locking means, said locator boom comprising a beam extending outwardly from said releasable locking means and toward said bone;

a cannulated drill sleeve moveably mounted to said support housing; and indexing means assembled to said support housing and having said cannulated drill sleeve releasably engaged therewith for movement of said cannulated drill sleeve between a first position, relative to said support housing, and a plurality of alternative positions, relative to said support housing, in response to a one-handed actuation of said indexing means;

(2) selecting a location on a second bone surface where a tunnel is to exit said bone and positioning said locator boom at that point;

(3) adjusting the angular relationship between said locator boom and said cannulated drill guide by (i) one-handedly moving said releasable locking means upwardly or downwardly relative to said cannulated drill sleeve, and (ii) one-handedly locking said releasable locking means to said support housing once a desired angular relationship has been established therebetween;

(4) one-handedly indexing said cannulated drill sleeve from a first position toward said selected point on said second bone surface until bone-engaging means disposed at a distal end of said drill sleeve contact said second bone surface; and (5) inserting said guidewire or drill through said cannulated drill sleeve until it is seated on said second bone surface.

24. A device according to claim 1 wherein said support housing includes a plurality of external surfaces, an internal cavity that is accessible from at least one of said surfaces, an upwardly extending curved radial rack, and a bore passing through said support housing, said bore being adapted for receiving said cannulated drill sleeve, and further wherein:

said releasable locking means comprise a locator boom housing adapted for engaging said curved radial rack, said locator boom housing including a thumb actuated locking lever that is pivotally biased to said locator boom housing so as to provide for a one-handed position adjustment of said locator boom housing upwardly or downwardly along said curved radial rack, said locking lever including a rack engaging portion so as to be in normally locking engagement with said curved radial rack; and said indexing means comprise a lock/release gripper plate pivotally fastened to an external end surface of said support housing, said lock/release gripper plate being spring biased outwardly relative to said external end surface so as to (i) normally grip said cannulated drill sleeve with an edge defined by a centrally positioned bore yet (ii) slidably release said cannulated drill sleeve when said lock/release gripper plate is urged toward said external end surface, thereby permitting said cannulated drill sleeve to be single-handedly advanced toward a target bone by pushing it through said support housing with one hand.

25. A device according to claim 2 wherein said bone engaging end lower surface comprises two downwardly extending pointed portions arranged in a double fang configuration.

* * * * *

UNITED STATES PATENT AND TRADEMARK OFFICE
CERTIFICATE OF CORRECTION

PATENT NO. : 5,458,602
DATED : October 17, 1995
INVENTOR(S) : E. Marlowe Goble et al.

It is certified that error appears in the above-indentified patent and that said Letters Patent is hereby corrected as shown below:

Claim 5, column 13, line 57, insert the word "rack" before the word --adapted--.

Claim 20, column 15, line 24, delete the period after the word --gripper--.

Claim 20, column 15, line 25, delete "fi)" and insert --(i)--.

Signed and Sealed this

Fifteenth Day of June, 1999

Attest:

Q. TODD DICKINSON

Attesting Officer

Acting Commissioner of Patents and Trademarks